United States Patent [19]
Hettiarachchi et al.

[11] Patent Number: 5,571,394
[45] Date of Patent: Nov. 5, 1996

[54] MONOLITHIC SENSOR SWITCH FOR DETECTING PRESENCE OF STOICHIOMETRIC $H_2/O_2$ RATIO IN BOILING WATER REACTOR CIRCUIT

[75] Inventors: Samson Hettiarachchi, Menlo Park; Maurice E. Indig, Fremont; Robert J. Law, Livermore, all of Calif.

[73] Assignee: General Electric Company, San Jose, Calif.

[21] Appl. No.: 437,269

[22] Filed: May 8, 1995

[51] Int. Cl.⁶ .................................................. G01N 27/26
[52] U.S. Cl. ..................... 204/400; 204/435; 205/775; 205/794.5
[58] Field of Search ..................... 204/433, 435, 204/153.21, 400; 205/775, 794.5

[56] References Cited

U.S. PATENT DOCUMENTS

| | | | |
|---|---|---|---|
| 3,113,048 | 12/1963 | Thompson | 204/284 |
| 3,154,477 | 10/1964 | Kesler | 204/284 |
| 4,166,020 | 8/1979 | Trampert | 204/435 |
| 4,252,124 | 2/1981 | Maurer et al. | 204/435 |
| 4,814,058 | 3/1989 | Bordenick | 204/435 |
| 4,948,492 | 8/1990 | Niedrach et al. | 204/435 |
| 4,978,921 | 12/1990 | Indig et al. | 324/446 |
| 5,043,053 | 8/1991 | Indig et al. | 204/421 |
| 5,192,414 | 3/1993 | Indig et al. | 204/400 |
| 5,217,596 | 6/1993 | Indig et al. | 204/435 |

OTHER PUBLICATIONS

"The Viability of pH Measurements in Supercritical Aqueous Systems", S. Hettiarachchi et al., J. Electrochem. Soc., vol. 139, No. 1, Jan. (1992).

*Primary Examiner*—T. Tung
*Attorney, Agent, or Firm*—James E. McGinness

[57] ABSTRACT

An electrode probe for measuring the electrochemical potential of a surface at a location of interest in a boiling water reactor. The probe has a monolithic sensor configuration built into a single stainless steel mineral insulated (MI) cable. This monolithic sensor can be used as a switch to detect when the appropriate concentration of dissolved hydrogen required to provide IGSCC mitigation is present at any location inside the reactor. Using the sensor switch, it is possible to in situ instantly determine the minimum hydrogen level required to reach the IGSCC protection potential. The sensor configuration consists of a metal/metal oxide/$ZrO_2$ sensor and a noble metal sensor in a combination wherein the outer sheath of a mineral insulated cable acts as the conductor for the noble metal and the central conductor of the MI cable acts as the conductor for the metal/metal oxide/$ZrO_2$. The metal/metal oxide/$ZrO_2$ sensor acts as a reference electrode in the BWR environment (i.e., at constant pH) and the noble metal sensor acts as a hydrogen electrode which responds to the dissolved hydrogen content in the BWR water.

20 Claims, 2 Drawing Sheets

MONOLITHIC SENSOR SWITCH FOR DETECTING PRESENCE OF STOICHIOMETRIC $H_2/O_2$ RATIO IN BOILING WATER REACTOR CIRCUIT

FIELD OF THE INVENTION

This invention relates to a rapid method of detecting the presence of the appropriate amount of hydrogen required to reach the irradiation-assisted stress corrosion cracking protection potential in water having a temperature of about 150° C. or greater. In particular, the invention relates to an electrochemical switch to be used in a light water nuclear reactor, for example, during the injection of hydrogen into the reactor water.

BACKGROUND OF THE INVENTION

Stress corrosion cracking (SCC) is a known phenomenon occurring in reactor components, such as structural members, piping, fasteners, and welds, exposed to high-temperature water. As used herein, SCC refers to cracking propagated by static or dynamic tensile stressing in combination with the reactor aqueous environment. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, crevice geometry, heat treatment, and radiation can increase the susceptibility of metal in a component to SCC.

It is well known that SCC occurs at higher rates when oxygen is present in the reactor water in concentrations of about 5 ppb or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the kinetic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration of $O_2$, $H_2O_2$, and $H_2$ is oxidizing and results in conditions that can promote intergranular stress corrosion cracking (IGSCC) of susceptible materials of construction. One method employed to mitigate IGSCC of susceptible material is the application of hydrogen water chemistry (HWC), whereby the oxidizing nature of the BWR environment is modified to a more reducing condition. This effect is achieved by adding dissolved hydrogen to the reactor feedwater. When the hydrogen reaches the reactor vessel, it reacts with the radiolytically formed oxidizing species on metal surfaces to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in the water. However, factors such as variations in water flow rates and the time or intensity of exposure to neutron or gamma radiation result in the production of oxidizing species at different levels in different reactors. Thus, varying amounts of hydrogen have been required to reduce the level of oxidizing species sufficiently to maintain the ECP below a critical potential required for protection from IGSCC in high-temperature water. As used herein, the term "critical potential" means a corrosion potential at or below a range of values of about −0.230 to −0.300 V based on the standard hydrogen electrode (SHE) scale. IGSCC proceeds at an accelerated rate in systems in which the ECP is above the critical potential, and at a substantially lower or zero rate in systems in which the ECP is below the critical potential. Water containing oxidizing species such as oxygen increases the ECP of metals exposed to the water above the critical potential, whereas water with little or no oxidizing species present results in an ECP below the critical potential.

It has been shown that IGSCC of Type 304 stainless steel (containing 18–20% Cr, 8–10.5% Ni, 2% Mn, remainder Fe) used in BWRs can be mitigated by reducing the ECP of the stainless steel to values below −230 mV(SHE). An effective method of achieving this objective is to use HWC. However, high hydrogen additions, e.g., of about 200 ppb or greater, that may be required to reduce the ECP below the critical potential, can result in a higher radiation level in the steam-driven turbine section from incorporation of the short-lived N-16 species in the steam. For most BWRs, the amount of hydrogen addition required to provide mitigation of IGSCC of pressure vessel internal components results in an increase in the main steam line radiation monitor by a factor of five to eight. This increase in main steam line radiation can cause high, even unacceptable, environmental dose rates that can require expensive investments in shielding and radiation exposure control. Thus, recent investigations have focused on using minimum levels of hydrogen to achieve the benefits of HWC with minimum increase in the main steam radiation dose rates.

An effective approach to achieve this goal is to coat, alloy or dope the stainless steel surface with palladium or other noble metal. The techniques used to date for palladium coating include electroplating, electroless plating, hypervelocity oxy-fuel, plasma deposition and related high-vacuum techniques. Palladium alloying has been carried out using standard alloy preparation techniques.

The most critical requirement for IGSCC protection of Type 304 stainless steel is to lower its ECP to values below the protection potential, i.e., −0.230 V(SHE). The manner in which this potential is achieved is immaterial, e.g., by alloying, doping or by any other method. It has been demonstrated that it is sufficient to dope the oxide film by the appropriate material (e.g., Pd) to achieve a state of lower ECP. It was shown in later work that a thickness of 200 to 300 Å of the doping element (Pd) is sufficient to impart this benefit of lower potential.

The presence of palladium on the stainless steel surface reduces the hydrogen demand to reach the required IGSCC protection potential of −0.230 V(SHE). It has been shown that Pd-containing stainless steel surfaces reach a negative potential of −0.500 V(SHE) as soon as the $H_2/O_2$ molar ratio exceeds the stoichiometric value of 2 (see FIG. 1). The exact potential of the Pd-containing stainless steel surface is determined by the Nernst equation depending on the system temperature and the dissolved excess hydrogen content in the water. The presence of palladium on the surface provides sufficient catalytic activity for $H_2$ and $O_2$ recombination to occur, which reduces the ECP of stainless steel surfaces below the potential required for IGSCC mitigation.

If noble metal technology involving coating, alloying or doping of noble metals such as palladium is used for IGSCC protection of stainless steels, then it is important to know the hydrogen injection levels required to reach stoichiometric or super-stoichiometric (i.e., $H_2/O_2$ molar ratios of 2 or greater) conditions.

The primary method used to quantify the levels of hydrogen injection needed to achieve IGSCC protection is the measurement of the ECP of the surface of interest in BWR water in a specific region. Electrochemical corrosion potential (ECP) monitoring is conventionally carried out employing paired electrochemical half-cell probes or electrodes which are mounted within the recirculation piping or in an external vessel which has its water source from the reactor water in the recirculation piping. The electrodes are accessed to the external environment through gland-type mountings or the like. Where the electrode system of interest involves the potential from a metal corrosion electrode, then the reference electrode can conveniently be a metal in equilibrium with a slightly soluble salt of the metal, which in turn is in equilibrium with a soluble salt having the same anion as the insoluble salt. The metal salt couple must be chemically stable. Accordingly, one of the thus-mounted probes which is configured as a reference electrode may be based, for example, on a silver/silver chloride half-cell reaction. Once the reference electrode half-cell is defined, the cell is completed with the sensing cell portion based upon a metal whose potential is to be measured, such as platinum or stainless steel. Verification of the reference electrode and/or the electrode pair is carried out by thermodynamic evaluation and appropriate Nernst equation-based electrochemical calculations in combination with laboratory testing within a known environment. When the measured ECP and value calculated from thermodynamics are in agreement, verification of the reference electrode performance is achieved.

Half-cell electrodes developed for use in reactor circulation piping traditionally have been configured with metal housings, high-temperature ceramics and polymeric seals such as Teflon brand polytetrafluoroethylene. These structures have performed adequately in the more benign and essentially radiation-free environments of recirculation piping.

over the recent past, investigators have sought to expand the ECP monitoring procedures to the severe environment of the fluid in the vicinity of the reactor core itself for the purpose of studying or quantifying the effect of hydrogen water chemistry adjustment in mitigating irradiation-assisted stress corrosion cracking (IASSC) as well as IGSCC. Within the reactor core, the monitoring electrode can be mounted, for example, with otherwise unemployed or in tandem with the traveling instrumentation probe of available local power range monitors and the like. The monitors are located in a severe, high-temperature (550° F.), high-radiation (typically $10^9$ R (rads) per hour gamma, $10^{13}$ R per hour neutron) water environments.

Thus, conventional ECP monitoring of BWR components has required the installation of at least two separate half-cell electrodes, namely, a platinum sensor that responds to hydrogen in the BWR water and a silver/silver chloride reference electrode that does not respond to hydrogen, with their associated cables. It would be an advance in the art if ECP monitoring could be performed using a sensor configuration requiring installation of only one cable for sensing and signaling the point of reversibility reaching stoichiometry with respect to hydrogen.

SUMMARY OF THE INVENTION

The present invention is a monolithic sensor configuration built into a single stainless steel mineral insulated (MI) cable. This monolithic sensor can be used as an electrochemical switch to detect when the appropriate concentration of dissolved hydrogen required to provide IGSCC mitigation is present at any location inside a BWR. Thus, using the sensor switch of the invention, it is possible to in situ instantly determine the minimum hydrogen level required to reach the IGSCC protection potential.

The sensor configuration consists of a metal/metal oxide/$ZrO_2$ sensor and a noble metal sensor in a combination wherein the outer sheath of a mineral insulated stainless steel cable acts as the conductor for the noble metal and the central conductor of the MI cable acts as the conductor for the metal/metal oxide/$ZrO_2$ sensor. The metal/metal oxide/$ZrO_2$ sensor acts as a reference electrode in the BWR environment (i.e., at constant pH) and the noble metal sensor acts as a hydrogen electrode which responds to the dissolved hydrogen content in the water.

Thus, under sub-stoichiometric conditions, i.e., in the presence of stoichiometrically less hydrogen compared to oxygen, the noble metal sensor detects a mixed potential controlled by both hydrogen and oxygen, whereas in the presence of excess hydrogen, the noble metal sensor becomes a reversible hydrogen sensor as determined by the amount of dissolved excess hydrogen in the water, assuming the pH of the BWR water remains constant. The potential of the noble metal sensor under these conditions can be predicted using the Nernst equation. Because the noble metal sensor becomes instantly reversible under excess hydrogen (i.e., super-stoichiometric) conditions, the combined sensor incorporating the metal/metal oxide/$ZrO_2$ reference electrode acts as a switch that instantly detects the excess hydrogen condition in the BWR environment.

Thus, the sensor arrangement in accordance with the present invention is able to detect the first indication of the reversibility of the noble metal sensor with respect to hydrogen, signaling the minimum hydrogen level required to achieve reversibility of a noble metal or a noble metal-coated, alloyed or doped stainless steel surface. Once the minimum or desirable hydrogen level has been determined, the injection of hydrogen into the reactor feedwater can be stopped. This eliminates the undesirable main steam line dose rate increases associated with the use of large excess of hydrogen.

The sensor switch of the present invention has a novel monolithic construction in that it is built as a single stainless steel MI cable. This greatly simplifies the installation of the sensor switch in a reactor circuit (in-core or ex-core), where the number of penetrations are strictly limited because of the reactor design and safety criteria. In addition, the method of using the sensor as a switch to detect reversibility greatly simplifies the hydrogen monitoring control technique applicable in a BWR. Furthermore,the sensor switch can be used for automated control of the hydrogen injection system based on the voltage difference ($\Delta E$) sensed between the two electrodes.

DETAILED DESCRIPTION OF THE PREFERRED EMBODIMENTS

Figure 2:
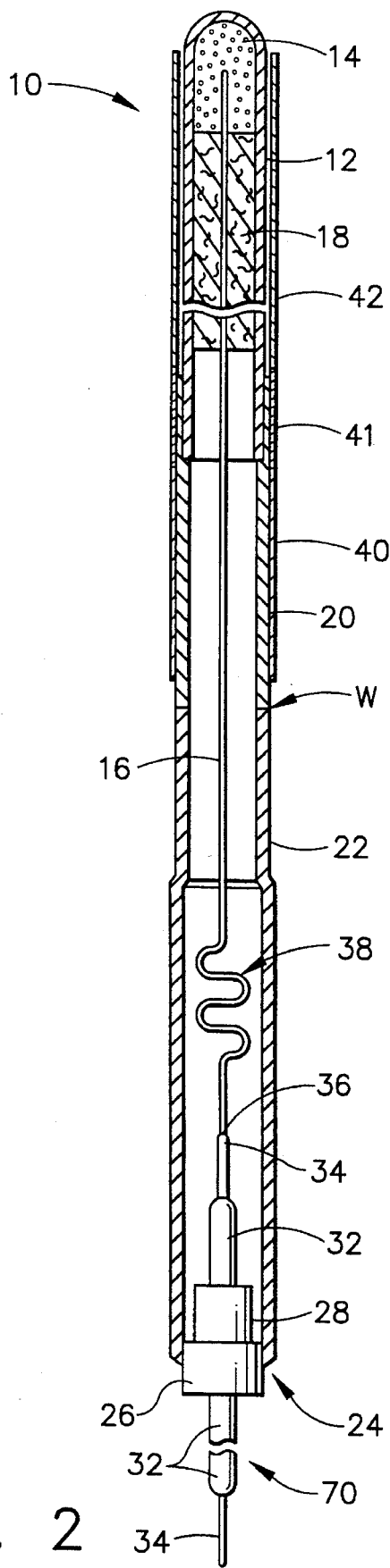
FIG. 2 is a sectional view of a sensor switch in accordance with the preferred embodiment of the invention.

Referring to FIG. 2, a radiation-hardened monolithic sensor switch 10 constructed in accordance with the preferred embodiment of the invention has a generally cylindrical structure. The center part of the sensor consists of crucible 12 made of zirconia ($ZrO_2$) partially stabilized with yttria ($Y_2O_3$). Crucible 12 is closed at one end and open at the other end. Alternatively, the zirconia can be any other partially stabilized zirconia or non-zirconia-based oxygen ion conducting material (provides constant potential at constant pH). The crucible 12 is filled with the appropriate metal/metal oxide powder 14 (e.g., $Ag/Ag_2O$, $Cu/Cu_2O$, $Fe/Fe_3O_4$ or Ni/NiO).

The metal/metal oxide powder is in intimate contact with a conductive wire 16 made of corresponding metal (e.g., Ag, Cu, Fe, Ni). Metal wire 16 has its distal end embedded in the metal/metal oxide powder mixture. The distal end of wire 16 is preferably bent into a hook or ring-like configuration which is pushed against the closed end of crucible 12.

Insulation packing 18, made, e.g., of zirconia felt, is tightly wound around the metal wire 16 and inside the crucible 12. This zirconia felt packing 18 serves to retain the metal/metal oxide powder packed in the crucible 12, and also electrically isolates the metal/metal oxide from contact with other metal housing components of the probe structure. In addition, after having packed crucible 12 with metal/metal oxide powder, packing 18, when inserted in the open end of crucible 12, wipes the interior surface of crucible 12 of any metal/metal oxide powder adhering thereto. Removing powder from the interior surface of crucible 12 adjacent its open end ensures electrical isolation of the metal/metal oxide powder from the metal housing components of the probe.

The zirconia crucible material provides the requisite oxygen ion conduction in high-temperature water and is chemically inert. The zirconia has a low corrosion rate that does not increase with pH shifts and is resistant to the erosion/corrosion that might exist in specific regions of the nuclear reactor. Accordingly, the zirconia material forming tube 12 is ideal for the in-core environment.

Zirconia crucible 12 is supported by circular cylindrical sleeve 20 formed of Kovar alloy. Kovar materials are a group of alloys having a characteristic of thermal expansion making it compatible with that of the zirconia material of crucible 12. Generally, Kovar material comprises 17–18% cobalt, 28–29% nickel, with the balance being mostly iron. One representative Kovar material comprises 53.8% Fe, 29% Ni, 17% Co and 0.2% Mn. This group of alloys, because they are ductile and do not become embrittled under conditions of ordinary use, including heating and annealing, are useful, for example, in sealing glasses. Other materials may be used in forming sleeve 20 provided that the coefficient of thermal expansion matches that of the zirconia crucible 12.

The outer cylindrical surface adjacent the open end of crucible 12 is a surface attachment region. This region of the yttria-stabilized zirconia crucible is joined to Kovar sleeve 20 by a technique known as active metal brazing wherein a small concentration of the active metal, e.g., titanium, becomes chemically bonded to the ceramic. The internal diameter of sleeve 20 is offset, for example, by counterboring, to provide an acceptance portion suited for receiving and being attached to the surface attachment region of crucible 12 for forming an intimate seal thereat.

The initially produced cylinder of Kovar for sleeve 20 is prepared by cleaning and inspecting, following which a post-machining annealing procedure is carried out. Following this annealing procedure, the component is nickel-plated, sintered and inspected. An intimate seal of the surface attachment region of zirconia crucible 12 with the acceptance portion of sleeve 20 is provided by painting the ceramic with titanium-silver paste and then brazing. This arrangement then completes a highly secure seal for sensor switch 10, as is required in view of the intended use thereof within the core region of a reactor.

The hollow interior of sleeve 20 provides an internal channel through which wire 16 may pass. To assure that wire 16 is insulated from the internal surfaces of sleeve 20, the wire is encased in a glass insulation. The glass insulation provides electrical insulation while remaining immune to the high temperatures encountered inside the reactor. A spring winding is formed in wire 16 as represented in general at 38. The spring section 38 protects against conductor breakage by allowing for expansion and contraction of wire 16 during heating and cooling cycles.

Kovar sleeve 20 is supported, in turn, by attachment to a circular cylindrical transition tube 22, which may be made of, e.g., Type 304 stainless steel. Transition tube 22 has a diameter equal to that of sleeve 20 and is attached at its transition end to a corresponding attachment portion of sleeve 20 by tungsten inert gas welding, e.g., using a tube welder, whereby weld W is formed. The hollow interior of transition tube 22 provides an internal channel representing a continuation of the channel of sleeve 20.

The lower end of transition tube 22 is formed in necked-down fashion to provide sealing end 24. End 24 is welded by tungsten inert gas welding to cylindrical stainless steel collar 26 of a cable connector assembly which has a ceramic support component 28 through which a mineral insulated cable 30 extends. Cable 30 may be provided with a stainless steel outer sheath 32 having alumina mineral insulation disposed inside with central conductor 34 centrally arranged therein. Sheath 32 is in electrical contract with a platinum sensing element. To provide an electric circuit completing connection with central conductor 34, the wire 16 is spot welded to the end of central conductor at 36. Thus, the central conductor 34 that protrudes out of the MI cable sheath 32 through a ceramic-to-metal seal is in electrical contact with the metal/metal oxide mixture inside the yttria-stabilized zirconia crucible 12.

In accordance with the preferred embodiment of the invention, the platinum sensing element consists of a platinum foil 40 and a platinum screen 42 which are connected in series as shown in FIG. 2. The platinum foil 40 is spot welded to the Kovar sleeve 20 and the platinum screen 42 is spot welded to the platinum foil 40 by the spot welding zone 41. An approximately 3-inch region of the Kovar sleeve 20 is covered with the platinum foil. The platinum screen 42 surrounds the cylindrical wall of zirconia crucible 12. In the case where crucible 12 and sleeve 20 are each circular in cross section, the platinum screen 42 in its assembled position will be concentric with the circular cylindrical wall of crucible 12.

Figure 1:
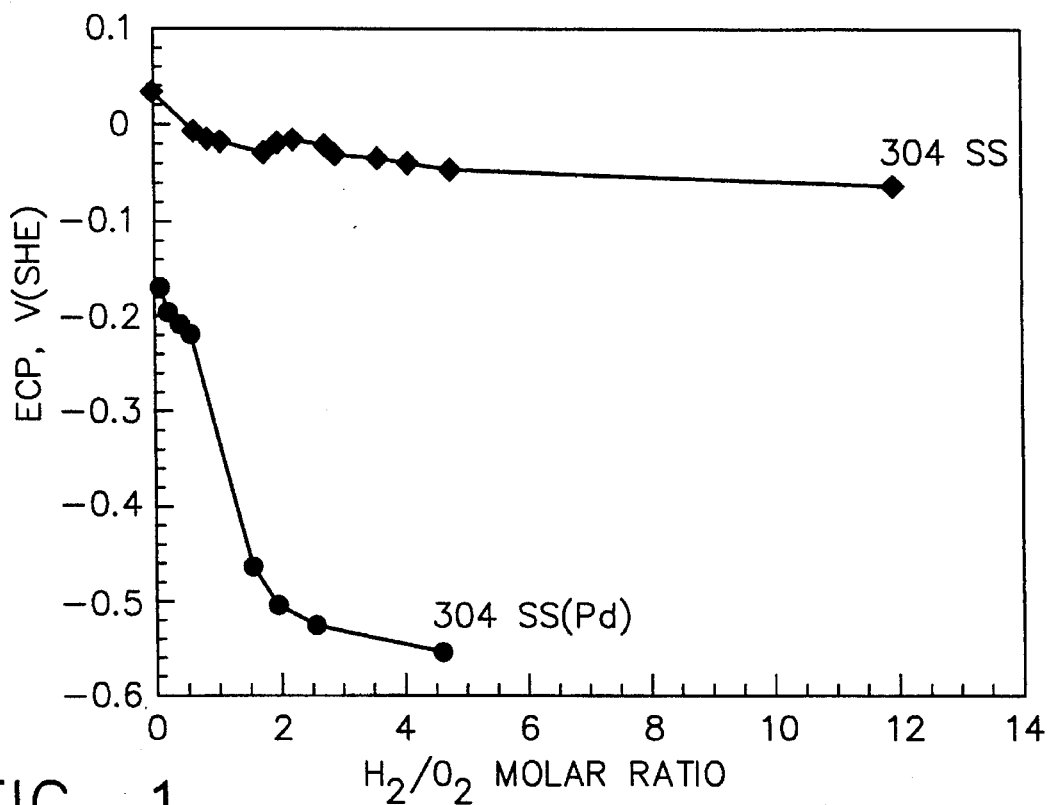
FIG. 1 is a plot showing the ECP response as a function of the molar ratio of hydrogen to oxygen for an undoped (♦) and a Pd-doped (●) Type 304 stainless steel specimen.
Figure 3:
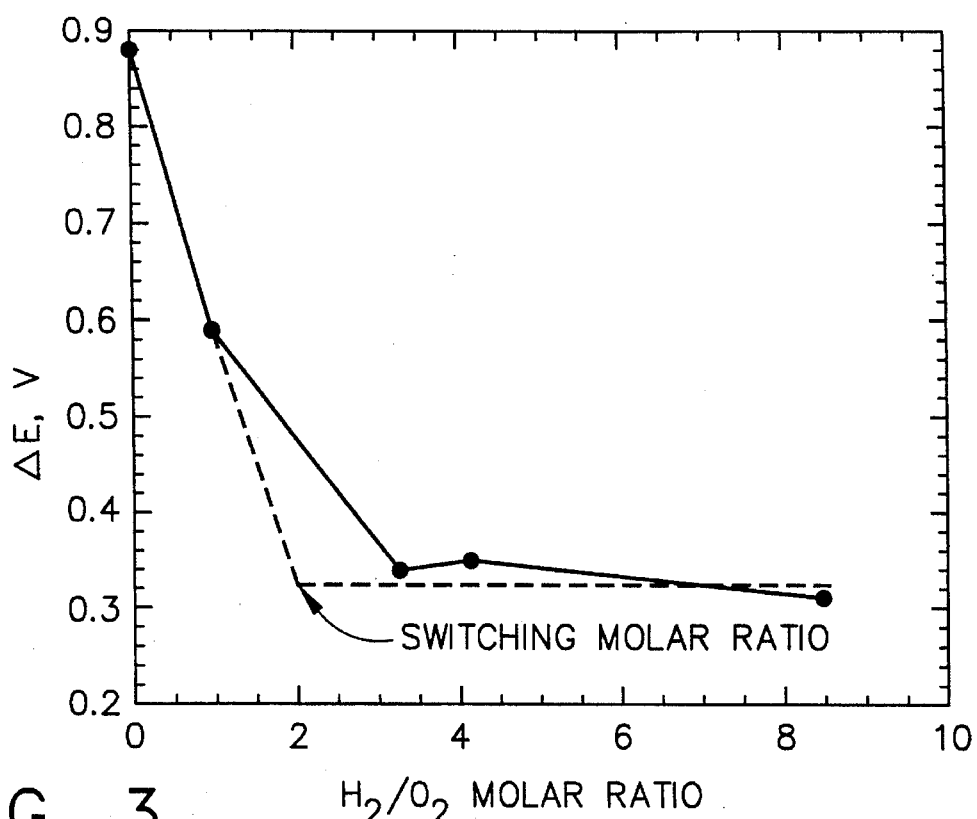
FIG. 3 is a plot showing the potential difference between a $Fe/Fe_3O_4/ZrO_2$ ($Y_2O_3$) reference electrode and a platinum hydrogen electrode constructed in accordance with the invention as a function of the molar ratio of hydrogen to oxygen in high-temperature water at 550° F.

The cable sheath 32 and central conductor 34 of MI cable 30 are electrically connected to the terminals of an electrometer located in the ambient environment outside the reactor. In the ambient environment the voltage signal corresponding to a potential difference equal to the potential of the reference electrode versus the potential of the platinum electrode is obtained. The potential difference between a $Fe/Fe_3O_4/ZrO_2$ ($Y_2O_3$) reference electrode and a platinum hydrogen electrode constructed in accordance with the invention is plotted as a function of the molar ratio of hydrogen to oxygen in high-temperature water at 550° F. The potential of the reference electrode is known from conventional thermodynamic analysis. As an example, the potential of the $Fe/Fe_3O_4/ZrO_2$ sensor in high-temperature water at 550° F. is –0.790 V(SHE). Therefore the ECP of the platinum hydrogen electrode can be calculated by adding the measured potential difference (a positive number) to the calculated reference electrode potential. Thus, the sensor arrangement in accordance with the preferred embodiment of the invention is able to detect the first indication of the reversibility of the noble metal sensor with respect to hydrogen, signaling the minimum hydrogen level required to achieve reversibility of noble metal or noble metal-coated, alloyed or doped stainless steel surfaces. Reversibility of the platinum sensor is indicated by a drop in the potential difference ($\Delta E$) by >0.5 V and reaching minimum constant value, as shown in FIG. 3. The dashed line in FIG. 3 corresponds to extrapolations based on the actual data.

The sensor response can be improved by electroplating the Kovar tube 20 and the stainless steel tube 22 with a noble metal (Pt, Pd, etc.) This reduces any deviation arising due to mixed potential effects.

In response to detection of the required minimum hydrogen level, hydrogen injection can be interrupted. This prevents any increase in the main steam line dose rate associated with the use of large excess of hydrogen.

The preferred embodiment described above is a monolithic sensor having two sensing terminals in one cable. A similar approach can be used to construct a multi-element sensor in a single cable wherein the cable consists of multiple conductors instead of a single conductor. The multiple elements can be insulated from each other and conducting wires from each element can be individually led to the central cable consisting of multiple conductors. Thus, the $Fe/Fe_3O_4/ZrO_2$ central reference electrode can monitor the potential of each of the sensing elements individually. An element that is of importance to BWRs is a $H_2O_2$ sensor so that the oxidizing potential of the BWR surfaces can be continuously monitored. All such variations of multi-element fabrication on a single cable are intended to be encompassed by the claims set forth hereinafter.

We claim:

1. An electrode probe for use in monitoring electrochemical potentials, comprising a hydrogen electrode, a first electrical conductor, means for electrically connecting said hydrogen electrode to said first electrical conductor, a reference electrode, a second electrical conductor, and means for electrically connecting said reference electrode to said second electrical connector, wherein said hydrogen electrode has openings, is made of noble metal and is arranged to surround said reference electrode with a gap therebetween.

2. The electrode probe as defined in claim 1, wherein said noble metal is platinum.

3. The electrode probe as defined in claim 1, wherein said hydrogen electrode comprises a cylindrical element and said reference electrode comprises a mass of metal/metal oxide powder packed inside a crucible made of an oxygen ion conducting material that provides constant potential at constant pH.

4. The electrode probe as defined in claim 3, wherein said cylindrical element and said crucible are each circular in cross section, and said cylindrical element is concentric with said crucible.

5. The electrode probe as defined in claim 3, wherein said oxygen ion conducting material comprises yttria-stabilized zirconia.

6. The electrode probe as defined in claim 3, wherein said cylindrical element comprises a platinum screen.

7. The electrode probe as defined in claim 6, wherein said means for electrically connecting said hydrogen electrode to said first electrical connector comprises a cylindrical sleeve made of electrically conductive material having a coefficient of thermal expansion compatible with the coefficient of thermal expansion of said oxygen ion conducting material, and a cylindrical foil made of platinum, said platinum foil being spot welded to said platinum metal screen and to said cylindrical sleeve.

8. The electrode probe as defined in claim 7, wherein said crucible is attached to said cylindrical sleeve by active metal brazing.

9. The electrode probe as defined in claim 1, wherein said hydrogen electrode comprises a cylindrical screen.

10. The electrode probe as defined in claim 9, wherein said means for electrically connecting said hydrogen electrode to said first electrical connector comprises a cylindrical sleeve made of electrically conductive material and a cylindrical foil made of said noble metal, said noble metal foil being spot welded to said noble metal screen and to said cylindrical sleeve.

11. An electrode probe for use in monitoring electrochemical potentials, comprising:

an insulated cable comprising a central conductor and a metal sheath surrounding said central conductor;

a hydrogen electrode electrically connected to said sheath; and a reference electrode electrically connected to said central conductor, wherein said hydrogen electrode has openings, is made of noble metal and is arranged to surround said reference electrode with a gap therebetween.

12. The electrode probe as defined in claim 11, wherein said noble metal is platinum.

13. The electrode probe as defined in claim 11, wherein said hydrogen electrode comprises a cylindrical element and said reference electrode comprises a mass of metal/metal oxide powder packed inside a crucible made of oxygen ion conducting material, said crucible being surrounded by said cylindrical element.

14. The electrode probe as defined in claim 13, wherein said cylindrical element and said crucible are each circular in cross section, and said cylindrical element is concentric with said crucible.

15. The electrode probe as defined in claim 13, wherein said oxygen ion conducting material comprises yttria-stabilized zirconia.

16. The electrode probe as defined in claim 13, wherein said cylindrical element comprises a screen.

17. The electrode probe as defined in claim 16, further comprising a cylindrical sleeve made of electrically conductive material having a coefficient of thermal expansion compatible with the coefficient of thermal expansion of said oxygen ion conducting material, and a cylindrical foil made of said noble metal, said foil being electrically connected to said screen and said cylindrical sleeve by spot welding.

18. The electrode probe as defined in claim 17, wherein said crucible is attached to said cylindrical sleeve by active metal brazing.

19. The electrode probe as defined in claim 11, wherein said hydrogen electrode comprises a cylindrical screen.

20. The electrode probe as defined in claim 19, further comprising a cylindrical sleeve made of electrically conductive material and a cylindrical foil made of said noble metal, said noble metal foil being electrically connected to said screen and said cylindrical sleeve by spot welding, and said cylindrical sleeve being electrically connected to said sheath.

* * * * *